United States Patent [19]

O'Farrell et al.

[11] Patent Number: 4,871,917

[45] Date of Patent: Oct. 3, 1989

[54] VEHICULAR MOISTURE SENSOR AND MOUNTING APPARATUS THEREFOR

[75] Inventors: Desmond J. O'Farrell; Kenneth Schofield, both of Holland; Mark L. Larson, Grand Haven; Karl-Heinz Hanft, Holland; Kenneth L. Schierbeek, Zeeland; Richard D. Bentley, Ravenna, all of Mich.

[73] Assignee: Donnelly Corporation, Holland, Mich.

[21] Appl. No.: 183,706

[22] Filed: Apr. 19, 1988

[51] Int. Cl.⁴ ............................................. G01N 21/41
[52] U.S. Cl. ................................. 250/341; 15/250 C; 250/339; 250/349
[58] Field of Search ....................... 250/339, 341, 349; 15/250 C; 318/444, 480, 483, DIG. 2

[56] References Cited

U.S. PATENT DOCUMENTS

| | | | |
|---|---|---|---|
| 3,307,095 | 2/1967 | Redmond, Jr. | 318/483 |
| 3,555,289 | 1/1971 | Sobkow | 307/10 R |
| 3,619,614 | 11/1971 | Yamaka | 250/352 |
| 3,649,898 | 3/1972 | Inoue | 318/483 |
| 3,660,659 | 5/1972 | Eisenman et al. | 250/352 |
| 3,689,814 | 9/1972 | Holt | 318/266 |
| 3,743,056 | 7/1973 | Zitelli et al. | 187/134 |

(List continued on next page.)

FOREIGN PATENT DOCUMENTS

| | | |
|---|---|---|
| 0175362 | 3/1986 | European Pat. Off. |
| 2101319 | 7/1972 | Fed. Rep. of Germany . |
| 2741653 | 3/1979 | Fed. Rep. of Germany . |
| 3206029 | 4/1983 | Fed. Rep. of Germany . |
| 3244767 | 6/1984 | Fed. Rep. of Germany . |
| 54-110529 | 8/1979 | Japan . |
| 57-22945 | 2/1982 | Japan . |
| 58-118436 | 7/1983 | Japan . |
| 58-185339 | 10/1983 | Japan . |
| 58-199253 | 11/1983 | Japan . |
| 59-14563 | 1/1984 | Japan . |
| 59-84141 | 5/1984 | Japan . |
| 59-85944 | 5/1984 | Japan . |
| 59-89250 | 5/1984 | Japan . |
| 59-100034 | 6/1984 | Japan . |
| 59-106348 | 6/1984 | Japan . |
| 60-78844 | 5/1985 | Japan . |
| 60-174348 | 9/1985 | Japan . |
| 60-174931 | 9/1985 | Japan . |
| 60-179648 | 9/1985 | Japan . |
| 60-216245 | 10/1985 | Japan . |
| 60-216246 | 10/1985 | Japan . |
| 1101441 | 1/1968 | United Kingdom . |
| 1150384 | 4/1969 | United Kingdom . |
| 1321221 | 6/1973 | United Kingdom . |
| 1382261 | 1/1975 | United Kingdom . |

OTHER PUBLICATIONS

U.S. patent application 073,469 by Hochstein, filed Jul. 15, 1987, entitled Electro-Optical Windshield Moisture Sensing, [U.S. Pat. No. 4,798,956].

Primary Examiner—Constantine Hannaher
Attorney, Agent, or Firm—Price, Heneveld, Cooper, DeWitt & Litton

[57] ABSTRACT

A moisture sensing assembly for controlling vehicle accessories such as windshield wipers is mounted on the inner surface of a vehicle window or windshield for detecting moisture on the outer window surface. A plurality of infrared energy emitting diodes and a sensor for receiving reflected infrared energy from the window and any moisture thereon are mounted at predetermined angles and spacing in a support. The support is biased against the window and enclosed in a protective housing detachably mounted to a window mounted plate preferably adjacent a rearview mirror on the front windshield. The support preferably includes an infrared energy monitoring sensor adjacent the emitting diodes which may be combined with or separate from an ambient infrared energy sensor. The monitoring and ambient sensors provide reference energy levels allowing compensation for varying diode output due to temperature and age and varying external vehicle light conditions.

48 Claims, 6 Drawing Sheets

U.S. PATENT DOCUMENTS

| | | | |
|---|---|---|---|
| 3,786,330 | 1/1974 | Inoue et al. | 318/483 |
| 3,794,847 | 2/1974 | Cadiou | 307/117 |
| 3,826,979 | 7/1974 | Steinmann | 324/61 R |
| 3,925,244 | 12/1975 | Nagasawa et al. | 250/372 |
| 3,977,792 | 8/1976 | Jumonji et al. | 356/209 |
| 4,010,383 | 3/1977 | Grassmann | 307/118 |
| 4,131,834 | 12/1978 | Blaszkowski | 318/483 |
| 4,139,801 | 2/1979 | Linares | 315/83 |
| 4,229,653 | 10/1980 | Uthe | 250/339 |
| 4,317,073 | 2/1982 | Blaszkowski | 318/483 |
| 4,339,698 | 7/1982 | Kearns | 318/444 |
| 4,355,271 | 10/1982 | Noack | 318/480 |
| 4,394,605 | 7/1983 | Terzawa | 318/280 |
| 4,463,294 | 7/1984 | Gibson | 318/313 |
| 4,476,419 | 10/1984 | Fukatsu et al. | 318/444 |
| 4,481,450 | 11/1984 | Watanabe et al. | 318/444 |
| 4,495,452 | 1/1985 | Boegh-Peterson | 318/444 |
| 4,542,325 | 9/1985 | Kobayashi et al. | 318/483 |
| 4,554,493 | 11/1985 | Armstrong | 318/444 |
| 4,588,935 | 5/1986 | Kaneiwa et al. | 318/483 |
| 4,589,771 | 5/1986 | Watanabe et al. | 356/38 |
| 4,595,866 | 6/1986 | Fukatsu et al. | 318/444 |
| 4,620,141 | 10/1986 | McCumber et al. | 318/443 |
| 4,636,643 | 1/1987 | Nakamura et al. | 250/338.1 |
| 4,636,698 | 1/1987 | Leclercq | 318/443 |
| 4,652,745 | 3/1987 | Zanardelli | 250/227 |
| 4,676,638 | 6/1987 | Yasuda | 356/237 |
| 4,689,536 | 8/1987 | Iyoda | 318/483 |
| 4,798,956 | 1/1989 | Hochstein | 250/341 |

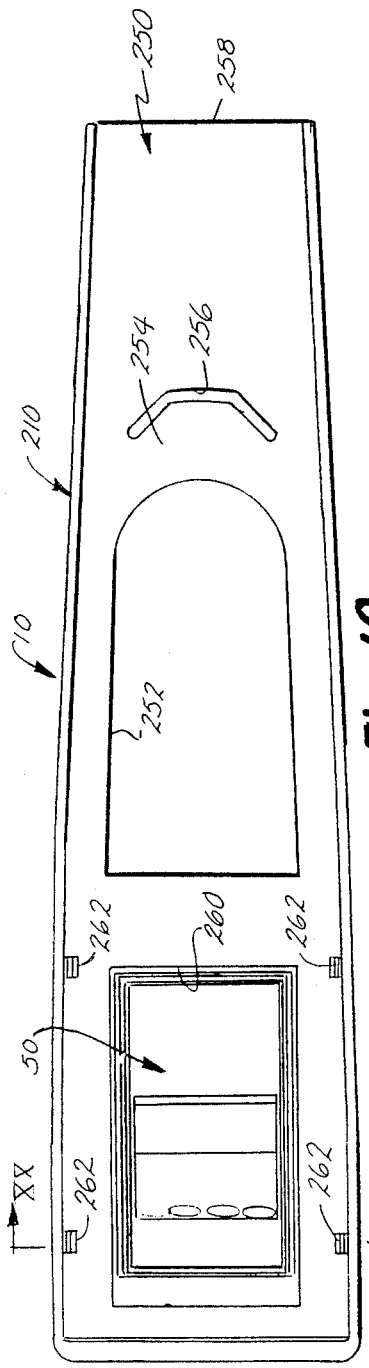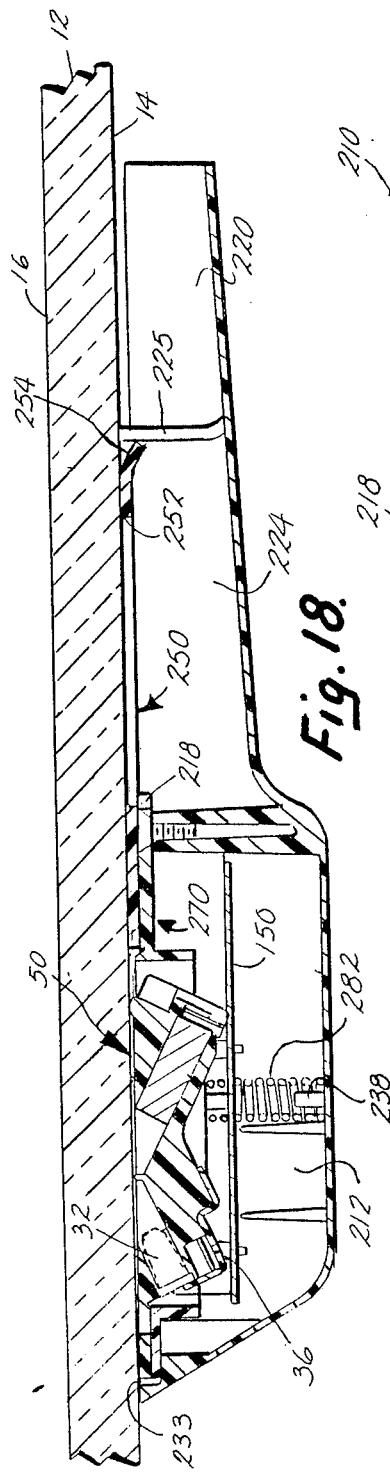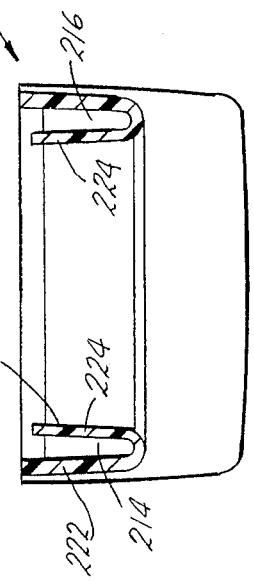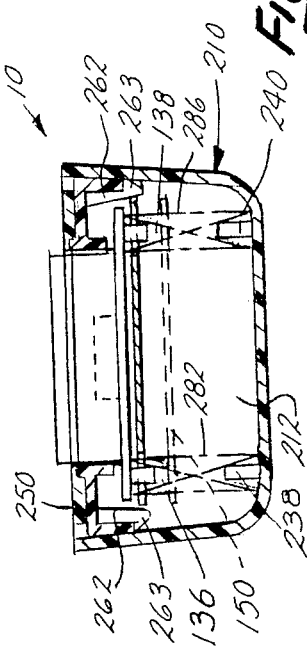

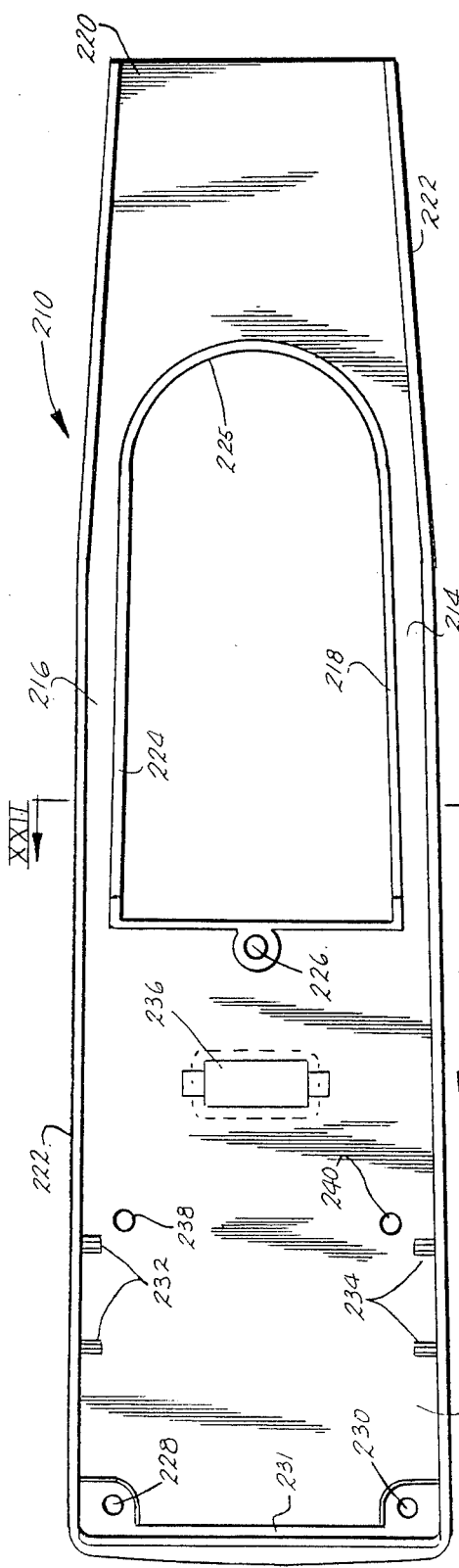
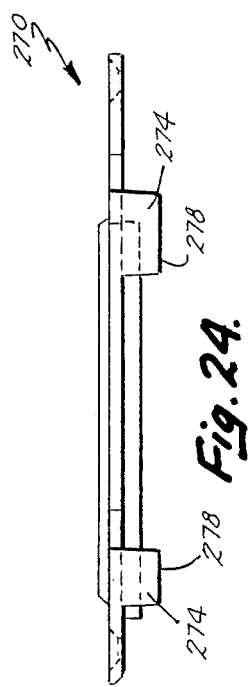
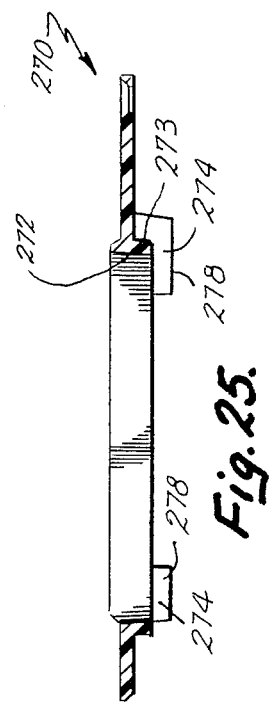
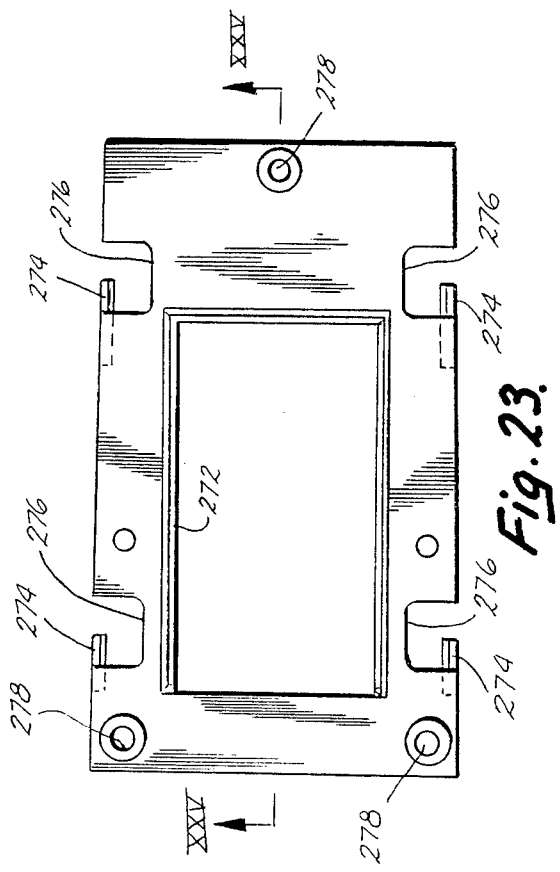

VEHICULAR MOISTURE SENSOR AND MOUNTING APPARATUS THEREFOR

BACKGROUND OF THE INVENTION

This invention relates to moisture sensors for detecting moisture and other particles such as rainfall, dew, dust and the like on vehicle windows for controlling vehicular accessories such as windshield wipers and the like. More particularly, the invention concerns an optical sensing apparatus and assembly for mounting the sensor on one side of a window panel for detecting moisture on the opposite side of a window panel while compensating for various environmental factors.

Various types of moisture sensing apparatus are known for use on vehicles to control accessories such as windshield wipers. These include resistance, capacitance, microwave, vibration and optical sensing devices. Many of these devices require application on the exterior of the vehicle. For example, resistance or capacitance measuring sensors typically require coatings or other structure on the exterior of a window or vehicle for physically contacting rainfall or moisture. These sensors require special production methods in manufacturing the window and significantly raise the window cost. Likewise, vibration sensors must be placed on the outside of the vehicle where rain, sleet, hail or the like can be sensed to create vibration for activation of the desired wiper or other accessory.

One moisture sensing device found particularly useful is an optical sensing apparatus employing an infrared emitter and detector which senses infrared energy emitted from inside the windshield or window and reflected back at decreased levels when moisture is present on the outside of the windshield to a detector also mounted on the interior of the vehicle. Such a sensor, which can be adapted to virtually any windshield without the need for special glass processing, is shown and described in U.S. patent application Ser. No. 073,496, filed July 15, 1987 by Peter A. Hochstein. That moisture sensor includes an emitter which emits pulses of radiant infrared energy toward the inside surface of a window at an incident angle. The radiant energy is refracted into the window at the inside air/window surface and reflected off the air/outside window surface back through the window where it is detected by a detector positioned along a reflection angle equal to the incident angle. The emitter and detector are spaced by a distance D as determined by the following formula where T is the thickness of the glass, n is the index of refraction for the glass, and $\theta$ is the angle of incidence and reflection of the infrared energy:

$$D = 2T \cos \theta \, (n^2 - \cos^2 \theta)^{\frac{1}{2}}$$

While this moisture sensing device has been found to be economical and reliable within a small predetermined temperature range, experimentation with the device has indicated that operation is inadequate over the typical automotive operating temperature range of $-40°$ C. to $+85°$ C. Indeed, it has been found that varying temperatures significantly affect the amount of infrared energy emitted thereby significantly changing the operational response of the moisture sensor incorporating such emitters.

In addition, tests have determined that typical infrared emitting elements used in the moisture sensor device of the above type also degrade in the amount of energy emitted over their lifetime. This also causes reduced operational effectiveness as infrared emission levels fall with age.

Further, it has been found that significant amounts of ambient light or infrared energy present in the environment in which the vehicle including the moisture sensor is operated can significantly affect and hinder operation of the accessory control using the device. For example, when the device is mounted on the front windshield of a vehicle, reflected light from the vehicle hood, or from snow which is present on the vehicle or on surrounding land or adjacent the road on which the vehicle travels can saturate the detecting system and prevent proper operation. Similarly, operation of a vehicle on inclines, at sunset, in the vicinity of large numbers of other vehicles whose head or tail lights are illuminated, or around street lights may cause premature operation of the unit and operation of the windshield wipers when no moisture is present.

Related problems regarding use of the moisture sensing units include maintaining proper geometrical relationship between the emitter and detector on the window or windshield in keeping with the above formula while allowing ease in removal and replacement of the unit for repairs or to allow replacement of the window or windshield if cracked or broken. Also, since the moisture sensing unit requires electrical power, an aesthetically pleasing housing was desired which could position the sensor within the sweep area of the windshield wipers while shielding and covering required electrical wiring.

SUMMARY OF THE INVENTION

Accordingly, the present invention provides a stabilized operation of a moisture sensing device such as that shown and described in U.S. Pat. No. 4,798,956 to Hochstein over a range of operational temperatures, over the lifetime of the unit, and in varying types of environmental conditions. The invention also maintains the sensing device in proper geometrical relationship adjacent a window surface and provides a protective enclosure which is detachably mounted to the window for removal and replacement when repairs or window replacement are necessary. In addition, the housing covers and shields any electrical wiring leading to the sensing unit.

In one form, the invention is a moisture sensing assembly for mounting on one surface of a window to detect and indicate moisture or other particles accumulated on the opposite side of the window. The assembly includes an emitter for emitting radiant energy toward the window, a detector for detecting and receiving radiant energy from the emitter after reflection and refraction by the window and any accumulated moisture or particles on the outside surface of the window. A support holds the emitter and detector in spaced angular relationship to one another. A mounting assembly releasably mounts the support on the inside window surface while biasing the support resiliently against the inside window surface such that the emitter is held at a predetermined incident angle and the detector is held at a predetermined reflection angle.

Preferably, the support for the emitter and detector includes a mounting block with apertures for receiving the emitter and detector extending at predetermined angles to a plane defined by contact surfaces for engaging the window or windshield surface. The support is biased by at least one spring extending between the block and the inside of a housing at a position between the contact surfaces. The support also preferably mounts a circuit board holding circuit elements for controlling operation of the emitter and detector.

The housing is slidably detachable from a mounting plate adhered to the inside window surface by a connecting assembly. The connecting assembly includes cooperating projections and flanges held in engagement by a releasable locking assembly. Preferably, the housing includes a channel-like wire cover extending from the housing to the vehicle interior roof headliner for covering any electrical wires leading from the moisture sensor to the vehicle.

In another aspect of the invention, a monitoring cell for monitoring the energy output from the emitter to provide a reference energy level based on the temperature and age of the emitter for comparison to the energy detected by the detector is included in the support. In addition, an ambient energy sensing cell may be included in the support for monitoring the ambient energy adjacent the assembly. The ambient sensor provides a reference energy level for comparison to the energy sensed by the detector such that high ambient energy levels may be distinguished from detected moisture. The monitoring cell may be combined with or separate from the ambient energy sensing cell. These emitter monitoring and ambient sensors compensate for varying emitter output due to temperature and age and varying external vehicle light conditions.

The present invention thus provides improved performance and mounting capabilities for the infrared energy type or other energy emitting moisture sensing units such as that disclosed in U.S. Pat. No. 4,798,956 mentioned above. The emitter and detector are mounted and maintained in proper angular relationship to the windshield glass for proper moisture detection. However, the mounting may be quickly released and detached from the window for repair replacement or window replacement. In addition, the sensing unit compensates for variations in temperature and age of the energy emitting sources which, in the preferred embodiment, are infrared emitting diodes which otherwise would radically affect operation. Likewise, ambient infrared energy levels are sensed for comparison to the energy sensed by the moisture detector to distinguish high ambient energy levels from detected moisture and other particles. Consequently, the present moisture sensing unit provides an accurate indication of moisture or other particles on the window without falsely responding to sunlight, surrounding street lights, automobile lights or other environmental conditions while operating effectively within the entire temperature range normally encountered by a vehicle throughout the lifetime of a vehicle.

These and other objects, advantages, purposes and features of the invention will become more apparent from a study of the following description taken in conjunction with the drawings.

BRIEF DESCRIPTION OF THE DRAWINGS

FIG. 18 is an enlarged, sectional view of the moisture sensing assembly of FIG. 1;

FIG. 19 is a plan view taken from the windshield mounted side of the moisture sensing assembly of FIGS. 1 and 18;

FIG. 20 is a sectional end view of the moisture sensing assembly of FIGS. 1, 18 and 19 taken along plane XX—XX of FIG. 19;

FIG. 21 is an enlarged plan view of the protective housing for enclosing the moisture sensing unit of the present invention;

FIG. 22 is a sectional view of the protective housing of FIG. 21 taken along plane XXII—XXII of FIG. 21;

FIG. 23 is a plan view of the housing retaining plate for mounting in the protective housing of FIGS. 21 and 22;

FIG. 24 is a side elevation of the retaining plate of FIG. 23; and

FIG. 25 is a sectional view of the retaining plate taken along plane XXV—XXV of FIG. 23.

DESCRIPTION OF THE PREFERRED EMBODIMENTS

Figure 1:
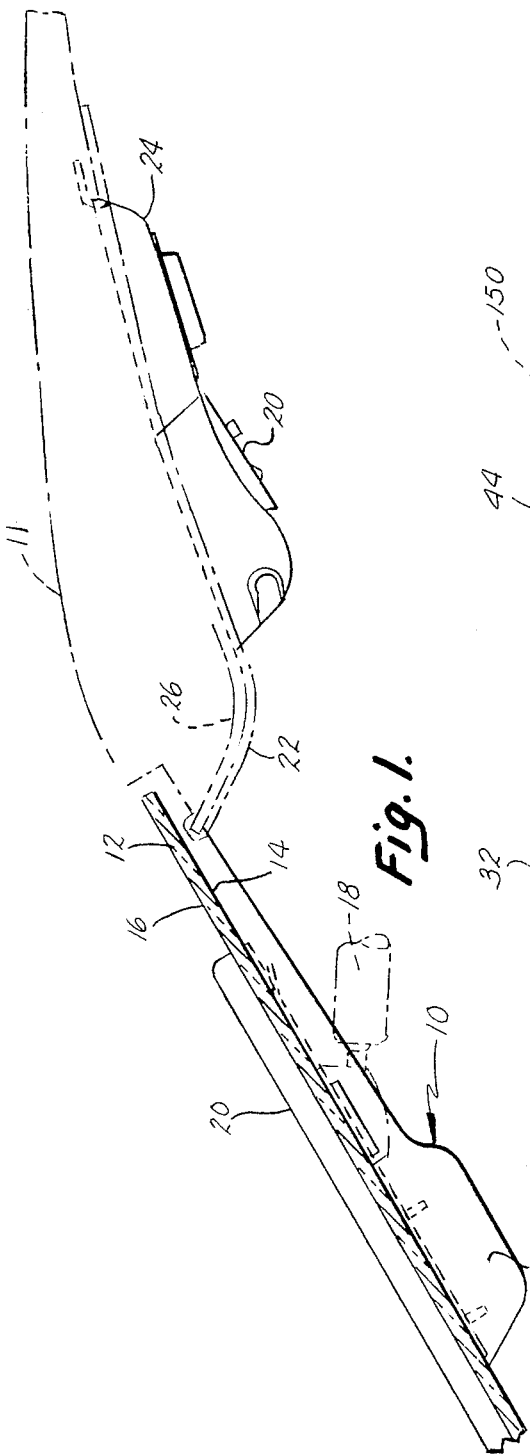
FIG. 1 is a side view of the moisture sensing assembly of the present invention mounted on a vehicle windshield within the wiper sweep area adjacent a rearview mirror mounting support.

Referring now to the drawings in greater detail, a first embodiment 10 of the moisture sensing assembly for controlling vehicle accessories such as windshield wipers is illustrated in FIG. 1. Assembly 10 is adapted for mounting on the inside surface of a window in vehicle 11 for sensing the presence of moisture such as rainfall, dew and the like or other particles such as dust on the exterior surface of the window. Preferably, the window is the front windshield 12 of vehicle 11 with assembly 10 being mounted on inside surface 14 for sensing the presence of moisture on the exterior surface 16. Assembly 10 is also preferably mounted adjacent rearview mirror support 18 and, in fact, surrounds that support which is also mounted on the interior surface 14 of the windshield 12 as explained more fully below. In order to function properly, it is necessary that the moisture sensing portion of assembly 10 be mounted within the sweep area of the windshield wipers 20 which clear the exterior surface 16 of windshield 12.

As is also seen in FIG. 1, and as more fully explained below, sensing assembly 10 includes a housing 210 which extends around rearview mirror support 18 upwardly to the interior roof headliner 22 of the vehicle where a header mounted switch console 24 is secured. An electrical wires 26 which extend from the moisture sensing unit of assembly 10 are concealed by elongated housing 210 and headliner 22 as they extend to console 24 which includes control switch assembly 28 for initiating operation of the moisture sensing assembly. The control switch assembly 28 could, of course, be located in the vehicle at other driver accessible locations such as on the turn signal stalk assembly on the steering column.

As shown in FIGS. 18-25, moisture sensing assembly 10 includes a moisture sensing unit 50 which is biased toward and urged resiliently against inside surface 14 of windshield 12. Sensing unit 50 and biasing structure are mounted within a detachable housing 210 which is mounted on inside windshield surface 14 via mounting plate 250. Sensing unit 50 includes a plurality of infrared energy emitting diodes 32 which emit and project infrared energy toward windshield glass 12 where, as explained below, the energy is refracted and reflected at the air/exterior glass interface back through the glass and into an infrared energy sensing photovoltaic cell 34 which converts the detected energy into an electrical signal. That signal is conveyed to an electronic control system on a circuit board 150. The circuit system includes solid-state, circuit control elements mounted thereon for controlling the operation of a windshield wiper system in response to the detected infrared energy. A photovoltaic cell 36 is also included adjacent diodes 32 to monitor their output and provide a reference voltage which compensates for output energy variations due to temperature and age. As explained below, other embodiments of the sensing unit may include an ambient energy sensing cell 36 to avoid false activation of the system due to environmental light conditions when no moisture is present.

In the preferred embodiments, sensing unit 50 is manufactured in accordance with the principles described in co-pending U.S. patent application Ser. No. 073,496, filed July 15, 1987 by Peter A. Hochstein entitled "ELECTRO-OPTICAL WINDSHIELD MOISTURE SENSING" now U.S. Pat. No. 4,798,956 the disclosure of which is hereby incorporated by reference herein. That application describes a moisture sensor and method for sensing moisture in which an infrared energy emitter emits pulses of infrared energy toward the inside surface of a windshield at a defined incident angle. The radiant energy is refracted into the window at the air/inside window surface and reflected off the air/outside window surface back through the window. The radiant energy is then detected by a photovoltaic detector at a reflection angle equal to the incident angle with respect to the glass surface. A support spaces the emitter and detector a distance D between the intersection of the axis of the emitter with the inside window surface and the intersection of the axis of the detector with the inside window surface which is determined by the following formula where T equals the thickness of the windshield glass, n is the index of refraction of the windshield glass and $\theta$ is the incident and reflection angle:

$$D = 2T \cos \theta (n^2 - \cos^2 \theta)^{-\frac{1}{2}}$$

The present moisture sensing unit 50 is an improved version of the moisture sensor described in U.S. Pat. No. 4,798,956 which compensates varying temperatures and environmental conditions over the life of the assembly.

Figure 2:
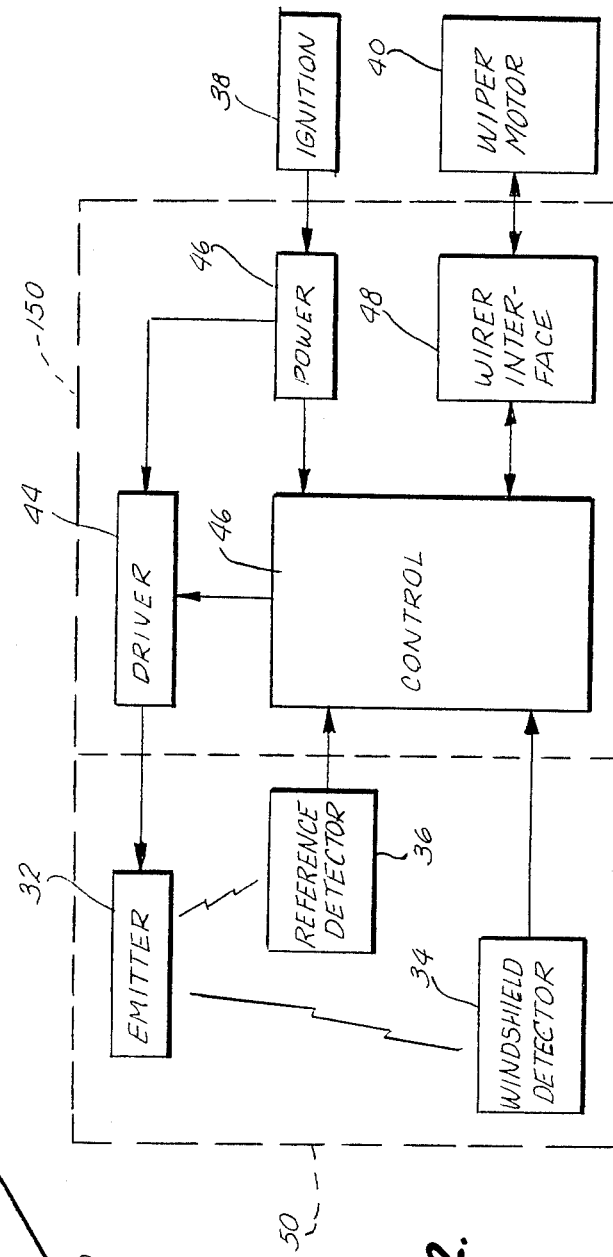
FIG. 2 is a schematic block diagram of the moisture sensing unit electrical control system and its connection to the vehicle electrical system and windshield wiper motor.
Figure 3:
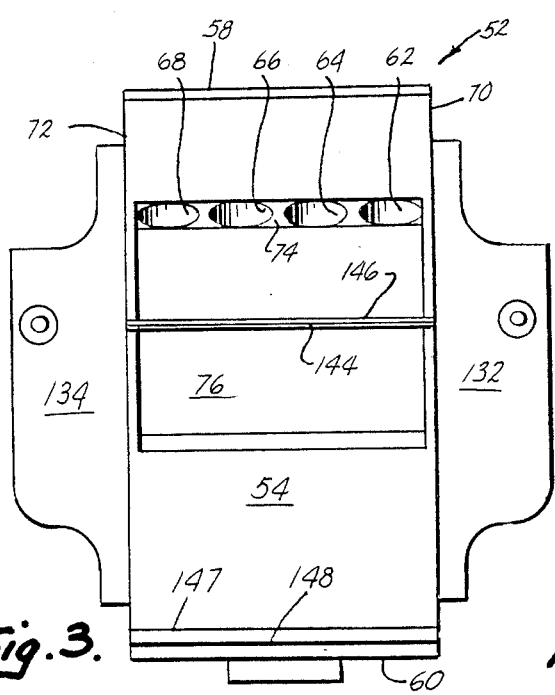
FIG. 3 is a top plan view of the emitter/detector mounting support block of the assembly of FIG. 1.

As shown in FIG. 2, the moisture sensing unit 50 of assembly 10 is powered through and controlled by an electronic circuit connected to the ignition 38 of vehicle 11 for control of a wiper motor or motors 40 in a windshield wiper system in the vehicle. When ignition 38 is switched on, DC power is supplied from a power circuit 42 to a driver circuit 44 which in turn activates infrared energy emitting diodes 32. Diodes 32 emit pulses of infrared energy which is detected after reflection and refraction at the windshield by detector 34 as well as by monitoring or reference detector 36. The signals from detectors 34, 36 are fed to a control circuit 46 which is also powered by power circuit 42 at the time ignition 38 is switched on. Control circuit 46 determines whether moisture is present on the exterior surface 16 of the windshield 12 or whether high ambient infrared energy levels are present which should be ignored. Likewise, control circuit 46 compensates for temperature variations affecting the output of emitter 32 as well as any decreased infrared energy emission levels due to the age of the emitting diodes 32 based on the reference energy levels detected by reference detector 36. When proper conditions have been met a determined by control circuit 46, wiper interface 48 and wiper motor 40 are activated to move wipers 20 across exterior surface 16 of the windshield to clear moisture and other particles therefrom. Thereafter, when detector 34 and control circuit 46 indicate no moisture, operation of the wiper motor 40 is shut down through the wiper interface 48.

The details of the operation of the elements of control circuit 46 and the moisture sensor assembly are described in co-pending, commonly assigned U.S. patent application Ser. No. 183,693 filed on even date herewith by Mark L. Larson, Desmond J. O'Farrell and Karl-Heinz Hanft entitled "CONTROL CIRCUIT FOR WINDSHIELD MOISTURE SENSING SYSTEM", the disclosure of which is hereby incorporated by reference herein.

Figure 6:
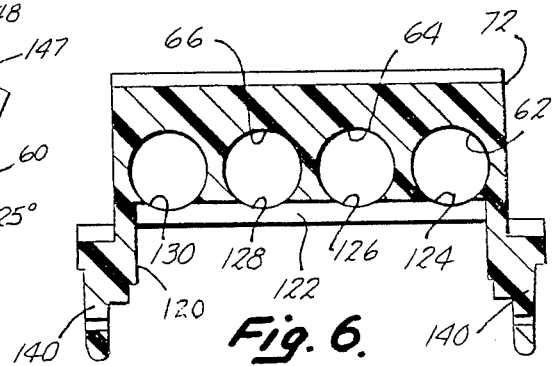
FIG. 6 is a sectional view of the emitter end of the mounting support block taken along plane VI—VI of FIG. 5.
Figure 7:
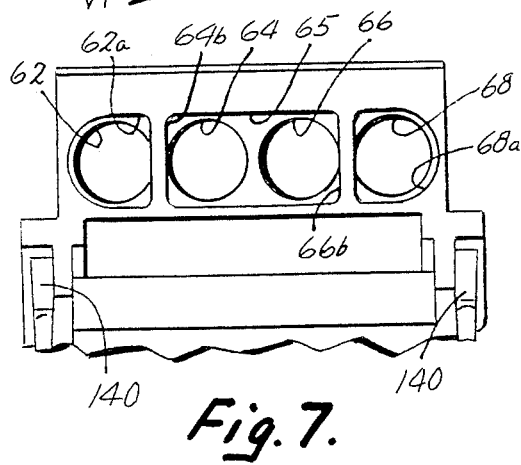
FIG. 7 is an end view of the emitter end of the mounting support block of FIGS. 3-5.
Figure 8:
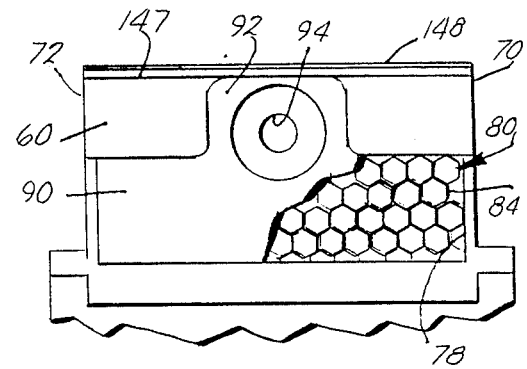
FIG. 8 is an end view of the mounting support block and detector cell retainer mounted thereon with portions of the detector cell retainer broken away to reveal the infrared energy collimator.
Figure 9:
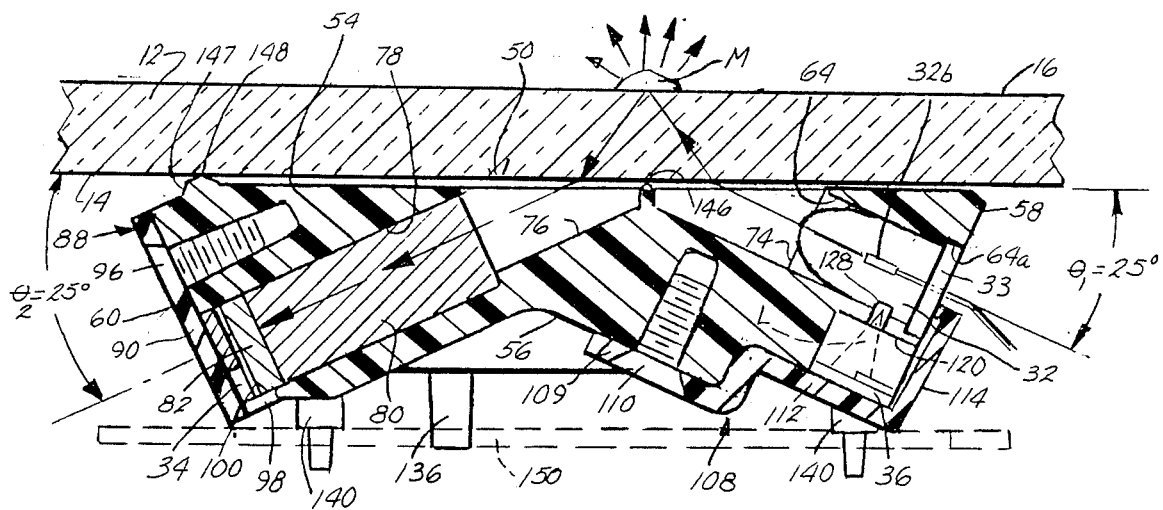
FIG. 9 is an enlarged, side sectional view of the emitter/detector mounting support block with infrared emitting diodes and an infrared sensing cell mounted therein.

Referring now to FIGS. 3-9, the first embodiment 50 of the moisture sensing unit is illustrated. Sensing unit 50 includes mounting support block 52 having a top surface 54 adapted to lie adjacent inside windshield surface 14, a bottom surface 56, a detector end surface 60 and an emitter end surface 58. Emitter and detector end surfaces 58, 60 preferably extend at an angle of approximately 25° to a line extending normal to the glass surface 14. Extending perpendicular to end surface 58 through the body of mounting block 52 in a direction equal to 25° from the top surface 54 (angle $\theta_1$ in FIG. 9) are a series of four infrared emitting diode receiving apertures 62, 64, 66 and 68. These apertures extend substantially parallel to side surfaces 70, 72 of the mounting block. Apertures 62 and 68 each include an enlarged recess 62a, 68a for receiving the base 33 of an infrared energy emitting diode 32 (FIG. 9). A surface 74 extending parallel to emitter end 58 approximately one-half way along apertures 62–68 defines the end of the enclosed portion of apertures 62–68 although the openings continue on through the top surface 54 of the mounting block. As is shown in FIG. 7, recesses 62a, 68a each include a flat face 62b, 68b for engaging a corresponding flat on base 33 of diode 32. These mating flat surfaces prevent rotation of the diodes in apertures 62 and 68 to maintain proper orientation of the emitting di 32b in each diode for proper infrared emission. A single recess 65 extends around apertures 64, 66 for bases 33 of the diodes 32 fitted within those apertures (FIG. 7). The outer ends 64b, 66b of recess 65 provide flat faces receiving the flats on diode bases 33 fitted in apertures 64, 66 also to prevent diode rotation.

Extending from the opposite emitter end 58 at an equivalent angle of 25° to the top surface 54 of mounting support block 52 is detector receiving aperture 76 including an enlarged portion 78 for receiving a collimator 80 and a portion of an infrared filter 82 adjacent detector end 60. Aligned with aperture 76, collimator 80 and filter 82 is infrared energy sensing photovoltaic cell 34 which has a thin, substantially planar rectangular shape and is held in position in alignment with aperture 76 by retainer 88.

Figure 13:
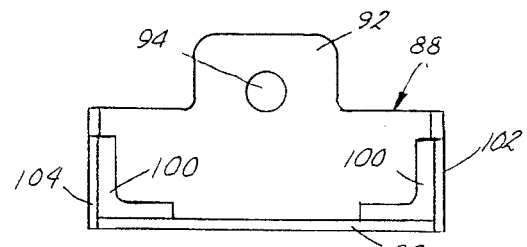
FIG. 13 is an end view of the detector cell retaining member for holding a detecting cell adjacent the detecting end of the mounting support block.
Figure 14:
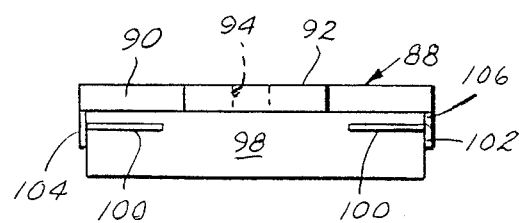
FIG. 14 is a top plan view of the detecting cell retaining member of FIG. 13.

As shown in FIGS. 13 and 14, retainer 88 includes a rear wall 90 having an upstanding flange 92 with aperture 94 therethrough for receiving a securing screw 96. A bottom wall 98 supports infrared filter 82 and infrared sensing photovoltaic cell 34 substantially parallel to rear wall 90. A pair of L-shaped upstanding flanges 100 separate cell 36 from infrared filter 82 as supported on bottom wall 98. Upstanding sidewalls 102, 104 close the ends of the retainer around the cell 34 and filter 82 although an elongated opening 106 extends downwardly in wall 102 through which leads from the photovoltaic cell 34 may be passed for connection to the electrical circuitry. Accordingly, when retainer 88 is secured with screw 96 against detector end 60 of the mounting block 52, photovoltaic cell 34 and filter 82 are held adjacent but slightly spaced from one end of collimator 80 which in turn is held against the narrowed portion of aperture 76. Such spacing prevents scratching and possible breakage of both cell 34 and filter 82.

Figure 10:
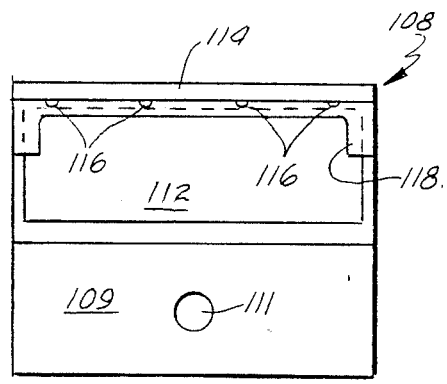
FIG. 10 is a top plan view of the diode retaining plate for holding diodes in the mounting support block.
Figure 11:
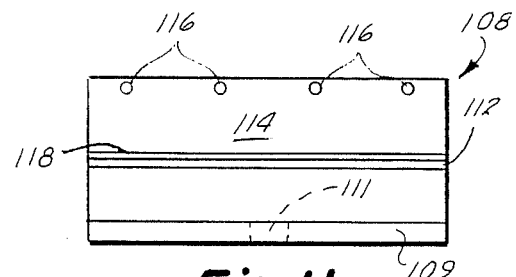
FIG. 11 is an end view of the diode retaining plate of FIG. 10.
Figure 12:
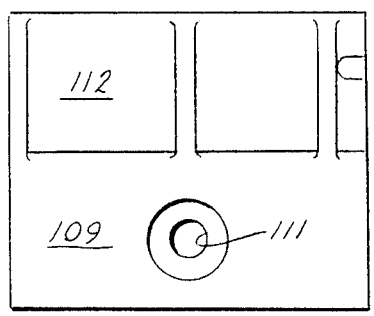
FIG. 12 is a bottom plan view of the diode retaining plate of FIGS. 10 and 11.

At the emitter end 58, diode retaining plate 108 is secured to the bottom wall 56 of the mounting block 52 by fastening screw 110 through aperture 111. Retainer 108 is configured to the bottom surface of the mounting block in stepped fashion and includes securing flange 109 and support wall 112 extending parallel to apertures 62–68 and a cantilevered retaining wall 114 extending substantially perpendicular to support wall 112. As shown in FIGS. 10–12, the inside surface of retaining wall 114 includes a series of four spaced, semi-circular protrusions 116. Each protrusion engages the outer surface of a diode base 33 as shown in FIG. 9. If the diode is formed to close tolerances by its manufacturer, base 33 will fit entirely within recesses 64a, 65 or 68a. However, if the diode is somewhat out of tolerance, bases 33 will project out of their recessed areas and resilient retaining wall 114 will be bent outwardly by contact of protrusions 116 with the diode bases. The resiliency of the retaining wall urges the diodes inwardly and keeps them tightly within their apertures to prevent vibration during use of the assembly.

As is also shown in FIGS. 9–12, retainer 108 supports photovoltaic infrared sensitive monitoring cell 36. Like photovoltaic cell 34, cell 36 is a thin, flat, rectangular, substantially planar element having cathode and anode sides with wire leads soldered to those opposite sides. A suitable photocell useful for cells 34, 36 is silicon photovoltaic cell obtained from Solar World Inc. of Colorado Springs, Colo. However, other infrared sensors could also be used such as photodiodes or photoresistors. Cell 36 is retained against vibration and movement on retainer 108 by thin, upstanding, substantially U-shaped wall 118 which spaces cell 36 at the greatest distance from diode 32 in recess 120 (FIGS. 4, 6, 9 and 15).

Figure 4:
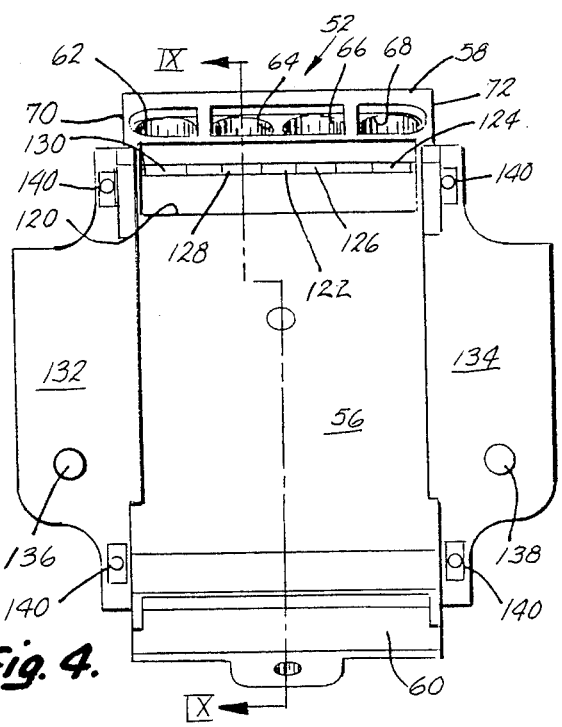
FIG. 4 is a bottom plan view of the emitter/detector mounting support block.
Figure 5:
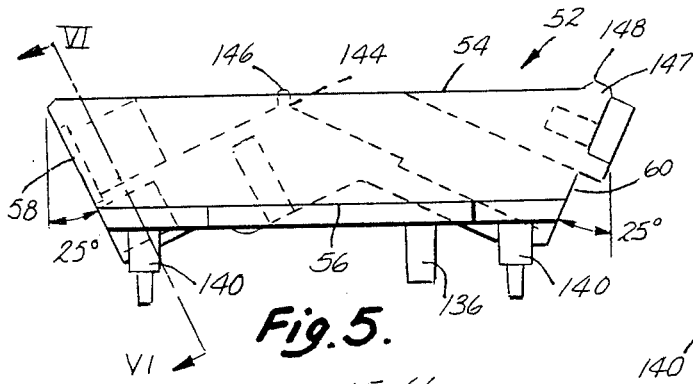
FIG. 5 is a side elevation of the mounting support block of FIGS. 3 and 4.

As will be understood from FIGS. 4 and 6, communication between the diode receiving apertures 62–68 and recess 120 to allow infrared energy from diodes 32 to strike monitoring cell 36 is provided by slot 122 which extends laterally across the mounting block 52 and includes openings 124, 126, 128 and 130 extending into each of the mounting apertures 62–68. Accordingly, as shown in FIG. 9, an area of infrared energy L from each of the diodes 32 may pass through openings 124–130 and slot 122 into recess 120 for illumination of cell 36 and resulting detection and monitoring of the diodes. As will be understood, the infrared energy from each of the four infrared energy emitting diodes 32 simultaneously strikes cell 36 such that cell 36 reads and detects all of that energy simultaneously and provides an output equivalent to the average output of all four energy emitting diodes.

As is best seen in FIG. 8, the collimator 80 is preferably formed from Hexcel (trademark) honeycomb material obtained from Hexcel Inc. of Bethel, Conn. and includes a plurality of integrally formed, parallel hexagonally-shaped tubes 84 extending completely through the collimator from one end to the other and, in this case, parallel to the detector apertures 76, 78. Preferably, the openings of tubes 84 are approximately 1/16" across in the preferred embodiment. Each tube is coated with a black paint to absorb stray infrared energy. In this configuration, collimator 80 limits the field of view of the photovoltaic cell 34 to that infrared energy which travels substantially parallel to the apertures 76, 78 and to the reflection angle of the infrared energy from emitting diodes 32 as explained hereinafter. Thus, collimator 80 substantially eliminates extraneous and extra infrared energy not originating with emitting diodes 32.

Preferably, filter 82 is thin, rectangular, substantially planar piece of filter glass which prevents passage of radiant energy below the infrared wavelengths, i.e., below 880 nanometers. A suitable glass is available from Hoya Optics Inc. of Sturbridge, Mass.

As shown in FIGS. 3–7 and 9, mounting support block 52 also includes a pair of laterally extending side flanges 132, 134 from which spring mounting posts 136, 138 extend downwardly. Also mounted on flanges 132, 134 and extending downwardly are a series of four circuit board mounting posts 140 at four spaced positions around the periphery of the mounting block 52. As shown in FIGS. 9 and 18, posts 140 receive a thin, substantially planar circuit board 150 through correspondingly spaced apertures in the circuit board. The reduced diameter portions of the mounting posts 140 are heat staked over the bottom surface of the circuit board to retain it permanently in place.

With reference to FIGS. 9 and 18, engagement of the mounting support block 52 with the inside surface 14 of windshield 12 will now be understood. Mounting block 52 includes a laterally extending upstanding wall 144 which is substantially perpendicular to top surface 54 and bisects the angle at which diode apertures 62-68 extend with respect to detector aperture 76. Wall 144 protrudes above the top surface 54 of block 52 and includes a knife edge 146 for engaging windshield surface 14. In addition, wall 144, being solid and opaque, blocks any infrared energy which might travel from apertures 62-68 into apertures 76, 78 without such energy first having traveled through windshield 12 and being reflected off the air/outer windshield surface 16 and back into detector apertures 76, 78 as shown in FIG. 9.

A second knife edge 148 is provided on laterally extending protrusion 147 adjacent the detector end 60 of the mounting block. Knife edges 146, 148 lie in a common plane such that mounting block 152 is positioned accurately with respect to the inside surface 14 of windshield 12 with diode apertures 62-68 and detector apertures 76, 78 lying at the correct angles of incidence and reflection as shown in FIG. 9 whenever those knife edges contact the windshield surface.

Accordingly, as will be understood from FIG. 9, pulsed infrared energy emitted by diodes 32 passes outwardly through the top surface 54 of block 52 to the air/glass interface at the inside surface of windshield 12. There, due to the index of refraction of the windshield glass, it is refracted outwardly to the outer air/glass surface at the exterior surface 16 of the windshield. In the absence of any moisture or dust particles on the outside of the windshield, such as after wiping, a substantial portion of the infrared energy is reflected by the air/outside windshield surface interface back into the glass where it is refracted back into detector apertures 76 and extends through collimator 80, filter 82 and onto photovoltaic detector cell 34. However, when moisture such as water drops M are present on the outside windshield surface, the infrared energy is scattered at the air/outside windshield surface interface such that a lesser amount of infrared energy is reflected back into photovoltaic cell 34. Such decreased amount of reflected energy is sensed by cell 34 and is indicated to control circuit 46 (FIG. 2) to initiate wiping action. Alternatively, should dust particles be present on the outside of the windshield, a greater amount of infrared energy would be reflected to photovoltaic cell 34 which would be indicated to control circuit 46 as a higher amount of energy. In the preferred embodiment, such signaling is ignored but could be used in other systems to activate windshield washing or spraying action in combination with wiping action to clean the windshield and remove the dust particles.

Figure 15:
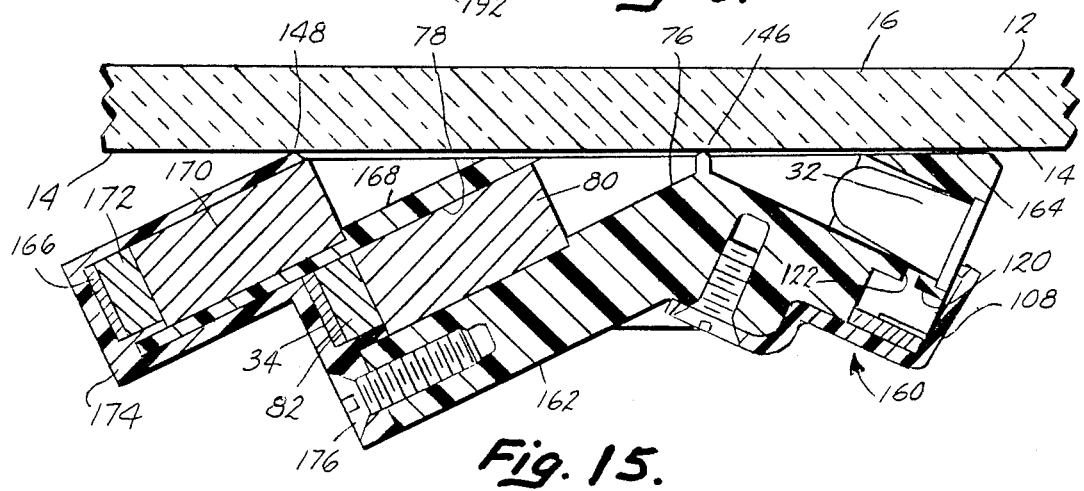
FIG. 15 is a side sectional view of an alternative embodiment of the moisture sensing unit of the present invention incorporating a diode monitoring and ambient energy sensing photovoltaic cell.

Referring now to FIG. 15, an alternative form 160 of the moisture sensing unit is illustrated where like parts to those shown in embodiment 50 bear like numerals. Sensing unit 160 is similar to embodiment 50 and includes a mounting support block 162 having an emitting end 164 including four aligned infrared emitting diodes 32 retained by retainer 108 and including a reference monitoring photovoltaic cell 36 held by retainer 108 and sensing infrared energy projected laterally from diodes 32 through recess 120 and slot 122 as in embodiment 50. Block 162 is supported on the inside surface of windshield 12 by knife edges 146, 148 lying in a common plane as in embodiment 50. However, in addition to detector photovoltaic cell 34 for receiving reflected, refracted infrared energy from emitter diodes 32 through collimator 80 and filter 82, embodiment 160 includes a third photovoltaic cell 166 substantially similar to cells 34, 36 for sensing ambient infrared energy emitted from objects in the environment around the sensing unit 160 and the vehicle in which it is mounted.

Cell 166 is mounted such that it extends substantially perpendicular to the direction of a second ambient energy detecting aperture 168 which extends parallel to detecting aperture 76. In addition, a second collimator 170, and filter 172, both identical to collimator 80 and filter 82, are positioned between the windshield glass and the photovoltaic cell 166 to limit infrared energy impinging on cell 166. Accordingly, ambient infrared energy sensing cell 166 provides an indicator signal to control circuit 46 (FIG. 2) indicating high levels of ambient infrared energy such that the control circuit will not activate wiper system 40, 48 at such times until a true signal indicating moisture on external surface 16 of the windshield is received in detector cell 34 from emitter diodes 32. Photovoltaic cells 34, 166 and filters 82, 172 are retained in place at the emitting end of mounting support block 162 by a configured retaining plate 174 held in place by fastening screw 176 as shown in FIG. 15.

Figure 16:
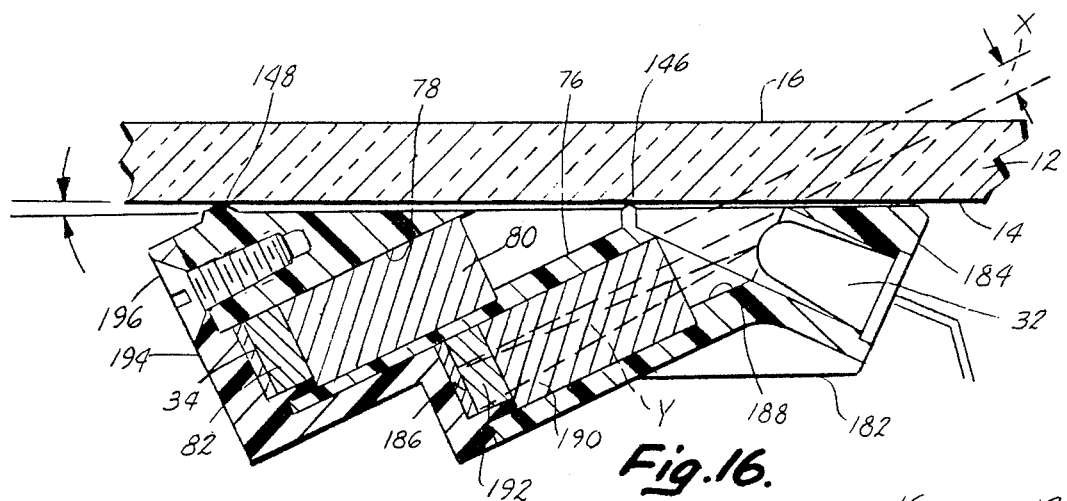
FIG. 16 is a side sectional view of a second alternative moisture sensing unit of the present invention incorporating a combined diode monitoring and ambient energy sensing photovoltaic cell.

A second alternative moisture sensing unit 180 is shown in FIG. 16. Unit 180 includes a mounting support block 182 for supporting a series of four emitting diodes 32 at emitting end 184. Diodes 32 emit infrared energy to windshield 12 which is reflected back to detector photovoltaic cell 34 through collimator 80 and filter 82 as in embodiments 50 and 160. However, intermediate the position of photovoltaic cell 34 and diodes 32 is mounted a second photovoltaic cell 186 identical to thin, flat cell 34 which simultaneously monitors infrared energy emitted by diodes 32 and senses ambient environmental infrared energy emitted in a direction parallel to detector aperture 76 along additional aperture 188 which is parallel to aperture 76. Photovoltaic cell 186 is preceded by collimator 190 and infrared energy filter 192 which are identical to collimator 80 and filter 82 as with photovoltaic cells 34 and 166. Cells 34 and 186, as well as filters 82 and 192 are held in place by retaining plate 194 which is secured to the detector end of mounting block 186 by fastening screw 196. Like mounting blocks 52 and 162, knife edges 146, 148 are included along the top surface of block 182 for proper contact with the inside surface 14 of windshield 12 to position the diodes 32 and detecting photovoltaic cell 34 in proper geometrical relationship as defined in U.S. Pat. No. 4,798,956 mentioned above. As will be understood from FIG. 16, photovoltaic cell 186 includes an area X from which ambient infrared energy is received parallel to aperture 188. Simultaneously, photovoltaic cell 186 receives light in the area Y from each of the emitting diodes 32 which project outwardly sufficiently beyond the edge of aperture 188 for emission of infrared energy to photovoltaic cell 186. Consequently, photovoltaic cell 186 senses infrared energy from each of the four emitting diodes thereby monitoring the average output of the four diodes while simultaneously sensing ambient environmental infrared energy levels for preventing operation of the wiper system 40, 48 without receipt of a proper moisture sensing signal from diodes 32 and photovoltaic cell 34.

Figure 17:
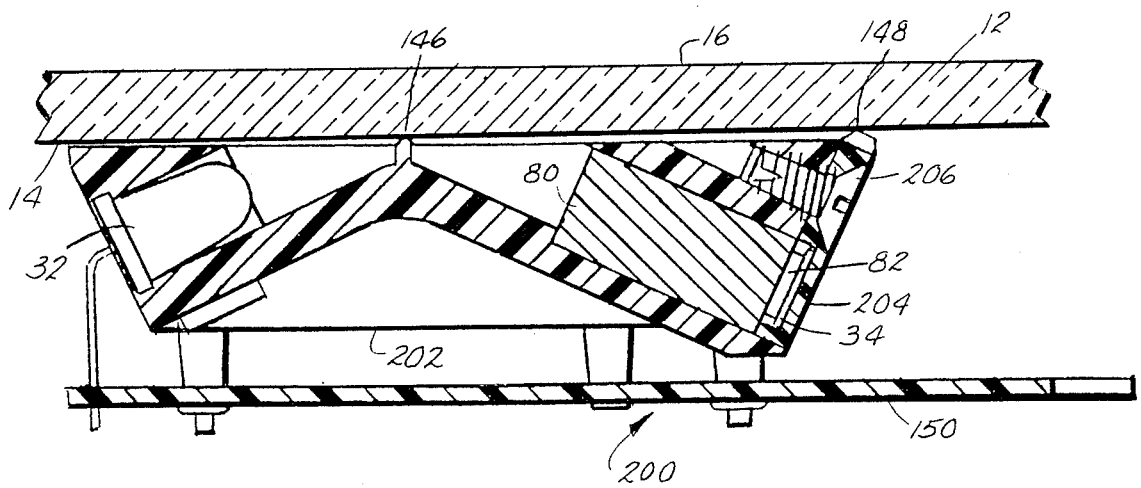
FIG. 17 is a side sectional view of a third alternative embodiment of the moisture sensing unit of the present invention including a circuit control board mounted thereon.

A third embodiment 200 of the moisture sensing unit useful in the present invention is shown in FIG. 17. Unit 200 is substantially simplified from embodiments 50, 160 and 180 and includes only the four infrared emitting diodes 32 and a single photovoltaic detecting cell 34, collimator 80 and infrared filter 82 in mounting support block 202. Again, knife edges 146, 148 position block 202 properly against the inside surface of the windshield while a simplified retainer plate 204 held in place by fastening screw 206 secures cell 34 in place. Embodiment 200 may be used in place of embodiment 50, 160 or 180 but does not provide any ambient environmental infrared energy level sensing or any monitoring of the infrared emitting diodes 32 to provide reference signals compensating for environmental energy or variation of energy output from diodes 32 due to temperature or age as do embodiments 50, 160 and 180.

Referring now to FIGS. 18–25, a protective housing and mounting assembly for supporting and detachably securing the moisture sensing units 50, 160, 180 or 200 against the inside surface 14 of windshield 12 is illustrated. As shown in FIGS. 18–20, the housing assembly includes an elongated housing 210 formed in one piece from an impact resistant resinous plastic material such as reinforced nylon. Housing 210 includes a moisture sensing unit receptacle 212 at its lower end, a bifurcated, hollow channel portion 214, 216 defining an aperture 218 extending through the housing 210, and an upwardly extending hollow channel portion 220 forming a wire cover adapted to extend to the headliner 22 interior of the vehicle roof. These sections of the housing are defined by an external, peripheral wall 222 extending around the entire housing except for its upper end through which electrical wires are adapted to exit and enter. Receptacle portion 212 is enlarged and extends farther outwardly from windshield glass 12 than does the bifurcated channel 214, 216 or upper wire cover channel 220 (FIG. 22).

Aperture 218 is defined by an interior upstanding wall 224 which is continuous and extends around the entire aperture as shown in FIG. 21. Curved, upper portion 225 of wall 224 is adapted to engage a resilient locking flange 254 for holding housing 210 on a mounting plate 250 as described hereinafter. Housing 210 also includes three fastening apertures 226, 228, 230 for securing a retaining plate 270 to the housing, opposed pairs of stiffening braces 232, 234, and may also include an aperture 236 extending through the outer wall of housing 210 in sensor receiving receptacle 212 for receiving an on-off switch should use of the assembly 10 be desired without a header console such as that shown at 24 in FIG. 1. Apertures 228, 230 are formed on shoulder 231 which defines a recess 233 inside wall 222 (FIG. 18). Upstanding spring mounting posts 238, 240 are also included for receiving springs for urging the moisture sensing unit 50, 160, 180 or 200 outwardly against the windshield glass when mounted therein.

With reference to FIGS. 18 and 19, housing 210 mates with an elongated mounting plate 250 also preferably formed from reinforced nylon. Mounting plate 250 includes a central aperture 252 and adapted for alignment with but is somewhat shorter than aperture 218 in housing 210. A resilient, outwardly extending locking flange 254 defined by angular slot 256 extends between the upper end 258 of mounting plate 250 and aperture 252. A moisture sensor receiving aperture 260 extends through the lower end of the plate 250. A series of four spaced, outwardly extending, J-shaped retaining projections 262 are formed integrally with plate 250 at the lower end of the plate for alignment with the moisture sensing unit receiving receptacle 212 of housing 210 (FIGS. 19 and 20). Each retaining projection 262 includes an enlarged head 263 forming a retaining shoulder which faces the windshield 12 and is spaced inwardly from the lateral side edges of plate 250 as shown in FIG. 20.

With reference to FIGS. 18 and 23–25, a housing retaining plate 270 is secured to housing 210 and cooperates with mounting plate 250 to retain housing 210 on plate 250 with moisture sensing unit 50, 160, 180 or 200 resiliently pressed against the inside windshield surface. Housing retaining plate 270, which is also preferably formed from reinforced nylon, is substantially planar and includes a central aperture 272 through which moisture sensing unit 50, 160, 180, 200 is received and protrudes against the inside windshield surface. Aperture 272 is defined by wall 273 which extends around the entirety of the aperture as shown in FIGS. 23 and 25. At the lateral side edges of plate 270 are four spaced, outwardly extending retaining flanges 274. Adjacent each retaining flange 274 is an L-shaped aperture or recess 276 allowing insertion and receipt of retaining projections 262 from mounting plate 250 therethrough for engagement with the outer surfaces 278 of flanges 274. Three fastener receiving apertures 278, spaced to correspond to apertures 226, 228 and 230 in housing 210, are provided for receiving fastening screws 280 for securing plate 270 in place within recess 233 at the open side of housing 210.

Accordingly, assembly of the moisture sensing assembly 10 will now be understood. One of the alternative moisture sensing units 50, 160, 180 or 200 is assembled to its appropriate circuit board 150 by heat staking posts 140 over the outer side of the circuit board. A pair of coil springs 282 is placed over locating posts 238, 240 on the interior of housing 210 in receptacle 212. The moisture sensing unit including circuit board 150 is then placed within receptacle 212 such that locating posts 136, 138 on the underside of the mounting support block are telescoped into the upper ends of springs 282 generally in alignment with locating posts 238, 240. Appropriate recesses in the side edges of circuit board 150 are provided to extension of the coil springs 282 therepast. Springs 282 thus are positioned longitudinally intermediate knife edges 146, 148 as shown in FIG. 18. Next, housing retaining plate 270 is assembled overtop the moisture sensing unit which projects through aperture 272 s that retaining flanges 274 project inwardly of housing receptacle 212 immediately adjacent the inside surfaces of the housing as shown in FIG. 20. Securing screws 280 are fastened in place to hold plate 270 within recess 233 of housing 210.

Housing 210, with retaining plate 270 and moisture sensing unit 50, 160, 180, 200 mounted therein, is then placed over the outer side of mounting plate 250 which has previously been adhered to the inside surface of windshield glass 12 with a suitable adhesive such as 458 Contact Tape Adhesive available from 3M Company of Minneapolis, Minn. In this connection, mounting plate 250 is typically received around and adjacent a rearview mirror support also adhered to windshield surface 14. A rearview mirror mounting arm is mounted on the support and extends through aperture 252 of plate 250. Thereafter, the housing assembly is aligned with the mounting plate 250 such that retaining projections 262 project through apertures 276 immediately adjacent the free ends of retaining flanges 274. In this position, resilient flange 254 is engaged by the top surface of wall portion 225. As the housing assembly is pressed toward windshield glass 12, resilient flange 254 is compressed to a planar position against the glass. The housing assembly including retaining plate 270 and moisture sensing unit may be slid upwardly toward the roof headliner 22 of the vehicle with the top of plate 270 engaging the bottom of plate 250 (FIG. 20) such that outer edges 278 of retaining flanges 274 engage the retaining projections 262 to hold the entire assembly against the windshield. In this procedure, as housing 210 is pressed toward the glass, the springs 282 are compressed by contact of the knife edges 146, 148 with the interior surface of the glass such that moisture sensing unit is pressed inwardly through aperture 272 as the springs compress. As the housing assembly is slid upwardly toward the vehicle roof headliner, the knife edges slide along the glass surface with moisture sensing unit being resiliently supported in a floating manner on springs 282 and resiliently urged outwardly against the glass to maintain the geometrical relationship of the emitting diodes and detector cells as described above. Simultaneously, with the sliding movement of the housing, resilient flange 254 slips past wall 225 and snaps outwardly into place as shown in FIG. 18 locking the housing 210 against return sliding movement and maintaining the assembly in place on the windshield.

After assembly of the housing unit to the mounting plate 250, the rearview mirror mounting arm 18 may be inserted through aperture 218 for engagement with the support member adhered to the windshield such that the rearview mirror support will project through the housing assembly. The moisture sensing unit 50, 160, 180 or 200 is thus supported below the rearview mirror while wire cove channels 214, 216, 220 extend upwardly toward the vehicle headliner above the rearview mirror. Any electrical wiring for supplying power to the moisture sensing unit passes through hollow channel 220 and around one side or the other of aperture 218 through passages 214, 216 to the circuit board and moisture sensing unit.

For removal of the housing unit and moisture sensing unit from the windshield, resilient flange 254 is manually pressed toward the windshield glass by inserting a tool or finger through aperture 218 until flange 254 is above wall 225. Housing 210 may then be slid downwardly such that wall 225 passes under resilient flange 254 and retaining projections 262 are released from the outer edges 278 of retaining flanges 274. The housing unit, including the moisture sensing unit, may thus be easily removed from the window for repair, replacement or window replacement as needed. The only additional procedure which may be necessary is to first remove rearview mirror assembly 18 from aperture 218 prior to removing moisture sensing assembly 10.

While several form of the invention have been shown and described, other forms will now be apparent to those skilled in the art. Therefore, it will be understood that the embodiments shown in the drawings and described above are merely for illustrative purposes, and are not intended to limit the scope of the invention which is defined by the claims which follow.

The embodiments of the invention in which an exclusive property or privilege is claimed are defined as follows:

1. A moisture sensing assembly for mounting on one surface of a window to detect and indicate moisture or other particles accumulated on the opposite surface of the window, the window having inside and outside surfaces, said assembly comprising:
    emitter means for emitting radiant energy toward the window;
    detector means for detecting and receiving radiant energy from said emitter means after reflection and refraction by the window and any accumulated moisture or particles on the outside surface of the window;
    support means for supporting said emitter means and detector means in spaced angular relationship to one another;
    a mounting member for attachment to the inside window surface;
    mounting means for engaging said mounting member and releasably mounting said support means on the inside window surface including biasing means for resiliently holding said support means against the inside window surface with said emitter means at a predetermined incident angle and said deflector means at a predetermined reflection angle; and
    releasable locking means on at least one of said mounting member and said mounting means for holding said mounting member and mounting means together until released.

2. A moisture sensing assembly for mounting on one surface of a window to detect and indicate moisture or other particles accumulated on the opposite surface of the window, the window having inside and outside surfaces, said assembly comprising:
    emitter means for emitting radiant energy toward the window;
    detector means for detecting and receiving radiant energy from said emitter means after reflection and refraction by the window and any accumulated moisture or particles on the outside surface of the window;
    support means for supporting said emitter means and detector means in spaced angular relationship to one another;
    mounting means for releasably mounting said support means on the inside window surface including biasing means for resiliently holding said support means against the inside window surface with said emitter means at a predetermined incident angle and said detector means at a predetermined reflection angle;
    said support means including a rigid mounting block having contact means along a predetermined plane for engaging the window surface, a first aperture extending at a first predetermined angle to said plane of said contact means, a second aperture extending at a second predetermined angle to said plane of said contact means, and radiant energy blocking means intermediate said first and second apertures for blocking passage of radiant energy directly between said apertures; said emitter means mounted in said first aperture; said detector means mounted in alignment with said second aperture.

3. The assembly of claim 2 wherein said mounting block includes a third angle between said first and second apertures and a top surface adapted to lie adjacent the inside window surface; said radiant energy blocking means including an upstanding wall which bisects said third angle and protrudes beyond said top surface; said wall having a free edge; said contact means including a first edge extending along said free end of said wall and a second edge adjacent an end surface of said mounting block and spaced from said first edge, said edges lying in said plane.

4. The assembly of claim 3 wherein said biasing means engages said mounting block at a position intermediate said first and second edges.

5. The assembly of claim 4 wherein said mounting means include a housing surrounding said mounting block; said biasing means including at least one spring extending between said housing and a rear surface of said mounting block.

6. The assembly of claim 2 including a plurality of additional apertures aligned in a row adjacent and parallel to said first aperture; said emitter means including a plurality of energy emitting sources, each of said sources mounted in one of said aligned apertures; said detector means including an infrared energy sensor.

7. The assembly of claim 6 including monitoring means for simultaneously monitoring and detecting the energy output from said plurality of sources whereby the average output from all said sources is detected.

8. The assembly of claim 7 including ambient energy sensing means for detecting and monitoring the ambient infrared energy adjacent said assembly.

9. The assembly of claim 6 including ambient energy sensing means for detecting and monitoring the ambient infrared energy adjacent said assembly.

10. The assembly of claim 2 wherein said emitter means includes an energy emitting source; said support means including a first retainer fastened to said mounting block for holding said energy emitting source in said first aperture.

11. The assembly of claim 10 wherein said detector means include an energy sensor; said support means including a second retainer fastened to said mounting block for holding said sensor in alignment with said second aperture.

12. The assembly of claim 11 including a collimator mounted in said second aperture intermediate said plane of said contact means and said sensor, said collimator limiting the field of view of energy entering said sensor by allowing only that energy which is substantially parallel to said reflection angle to impinge on said sensor.

13. The assembly of claim 12 including a filter for preventing radiant energy below a predetermined wavelength from reaching said sensor, said filter being mounted between said collimator and said sensor in alignment with said second aperture.

14. The assembly of claim 13 including a plurality of additional apertures aligned in a row adjacent and parallel to said first aperture; a plurality of infrared energy emitting diodes, each diode mounted in one of said aligned apertures; said diodes and apertures including cooperating means for preventing rotation of said diodes in said aligned apertures; said first retainer including means engaging each of said diodes for holding said diodes in said aligned apertures.

15. A moisture sensing assembly for mounting on one surface of a window to detect and indicate moisture or other particles accumulated on the opposite surface of the window, the window having inside and outside surfaces, said assembly comprising:

emitter means for emitting radiant energy toward the window;

detector means for detecting and receiving radiant energy from said emitter means after reflection and refraction by the window and any accumulated moisture or particles on the outside surface of the window;

support means for supporting said emitting means and detector means in spaced angular relationship to one another;

mounting means for releasably mounting said support means on the inside window surface including biasing means for resiliently holding said support means against the inside window surface with said emitter means at a predetermined incident angle and said detector means at a predetermined reflection angle; and a circuit board; said support means including means for mounting said circuit board thereon, said circuit board including circuit elements for controlling operation of said emitter and detector means.

16. A moisture sensing assembly for mounting on one surface of a window to detect and indicate moisture or other particles accumulated on the opposite surface of the window, the window having inside and outside surfaces, said assembly comprising:

emitter means for emitting radiant energy toward the window;

detector means for detecting and receiving radiant energy from said emitter means after reflection and refraction by the window and any accumulated moisture or particles on the outside surface of the window;

support means for supporting said emitter means and detector means in spaced angular relationship to one another;

mounting means for releasably mounting said support means on the inside window surface including biasing means for resiliently holding said support means against the inside window surface with said emitter means at a predetermined incident angle and said detector means at a predetermined reflection angle;

said mounting means further including a housing for enclosing said support means, a mounting plate adapted for attachment to the inside window surface, and connecting means on said housing for slidably engaging said mounting plate.

17. The assembly of claim 16 including channel means extending from said housing for covering an electrical wires leading from said support means to the vehicle.

18. The assembly of claim 17 wherein said housing and channel means define an aperture therethrough for receiving a rearview mirror mounting assembly when said assembly is mounted on a vehicle windshield.

19. The assembly of claim 16 wherein said connecting means include a retaining plate fastened to said housing, guide means on said mounting plate for slidably receiving said retaining plate; a plurality of retaining projections extending from said mounting plate at spaced positions, and a plurality of spaced flanges on said retaining plate at positions corresponding to said positions of said retaining projections for slidably engaging said retaining projections and retaining said support means, housing, and retaining plate as a unit to said mounting plate when said retaining plate and housing are slid with respect to said mounting plate on said guide means.

20. The assembly of claim 19 wherein said retaining plate includes a first aperture for receiving said support means and an additional aperture adjacent each of said spaced flanges for receiving said retaining projections therethrough; said support means extending through said first aperture as urged by said biasing means for engagement with the window surface.

21. The assembly of claim 20 including a first member spaced from said retaining plate on said housing and a resilient locking member on said mounting plate for releasably engaging said first member for preventing sliding movement and release of said spaced flanges from said retaining projection until manually released from engagement with said first member.

22. The assembly of claim 16 including releasable locking means on said mounting plate for engaging a portion of said housing to hold said housing and mounting plate together until released.

23. A moisture sensing assembly for mounting on one surface of a window to detect and indicate moisture or other particles accumulated on the opposite surface of the window, the window having inside and outside surfaces, said assembly comprising:
  emitter means for emitting radiant energy toward the window;
  detector means for detecting and receiving radiant energy from said emitter means after reflection and refraction by the window and any accumulated moisture or particles on the outside surface of the window;
  support means for supporting said emitter means and detector means in spaced angular relationship to one another;
  mounting means for releasably mounting said support means on the inside window surface including biasing means for resiliently holding said support means against the inside window surface with said emitter means at a predetermined incident angle and said detector means at a predetermined reflection angle; and
  monitoring means in said support means for monitoring energy output from said emitter means to provide a reference energy level for comparison to the energy detected by said detector means.

24. The assembly of claim 23 including ambient energy sensing means in said support means for monitoring the ambient energy adjacent said assembly to provide a reference energy level for comparison to the energy detected by said detector means to distinguish high ambient energy levels from detected moisture or other particles.

25. The assembly of claim 24 wherein said monitoring means includes said ambient energy sensing means, said monitoring means and said ambient energy sensing means being mounted in said support means adjacent said detector means.

26. The assembly of claim 25 wherein said monitoring means and ambient energy sensing means include a sensor sensitive to infrared radiation.

27. The assembly of claim 24 wherein said ambient energy sensing means includes a sensor sensitive to infrared radiation.

28. The assembly of claim 23 wherein said monitoring means include a sensor sensitive to infrared radiation; said detector means also including a sensor sensitive to infrared radiation.

29. A moisture sensing assembly for controlling vehicle accessories such as windshield wipers comprising:
  a moisture sensing unit for engaging on one surface of a vehicle window to detect and indicate moisture or other particles accumulated on the opposite window surface;
  mounting means for attachment to the one window surface;
  housing means for releasably supporting and enclosing said sensing unit on the vehicle window, said housing means including means for connection to said mounting means; and
  wire cover means on said housing means for covering and shielding any electrical wires which extend from said sensing unit to other portions of the vehicle.

30. A moisture sensing assembly for controlling vehicle accessories such as windshield wipers comprising:
  a moisture sensing unit for engaging on one surface of a vehicle window to detect and indicate moisture or other particles accumulated on the opposite window surface;

31. The assembly of claim 30 wherein said housing means includes a one-piece housing having a hollow receptacle for said moisture sensing unit, a bifurcated hollow channel defining said aperture, and a hollow channel portion which, together with said bifurcated channel, defines said wire cover means.

32. A moisture sensing assembly for controlling vehicle accessories such as windshield wipers comprising:
  a moisture sensing unit for engaging on one surface of a vehicle window to detect and indicate moisture or other particles accumulated on the opposite window surface;
  housing means for releasably supporting and enclosing said sensing unit on a vehicle window; and
  wire cover means for covering and shielding any electrical wires which extend from said sensing unit to other portions of the vehicle;
  said housing means including a housing, a mounting plate adapted for attachment to the inside window surface, and connecting means on said housing for releasably engaging said mounting plate; said moisture sensing unit mounted on said housing.

33. The assembly of claim 32 including releasable locking means for preventing disengagement of said connecting means from said mounting plate until manually released.

34. A moisture sensing assembly for mounting on one surface of a window to detect and indicate moisture or other particles accumulated on the opposite side of the window, the window of the type having inside and outside surfaces, said assembly comprising:
  emitter means for mounting adjacent the inside surface of a window to emit radiant energy toward the window at an incident angle;
  detector means for mounting adjacent the inside surface of the window to detect and receive radiant energy from the emitter means at a reflection angle after reflection and refraction by the window and any accumulated moisture or particles on the outside surface of the window;
  monitoring means for monitoring energy output from said emitter means to provide a reference energy level for comparison to the energy detected by said detector means;
  ambient energy sensing means for monitoring the ambient energy adjacent said assembly to provide a reference energy level for comparison to the energy detected by said detector means to distinguish high ambient energy levels from detected moisture or other particles; and support means for supporting said emitter means and detector means in spaced, angular relationship to one another, for mounting said monitoring means in position to receive radiant energy emitted by said emitter means, and for mounting said ambient energy sensing means for receiving ambient energy from generally the same direction as viewed by said detector means.

35. The assembly of claim 34 wherein said emitter means include infrared radiation emitting means for emitting infrared radiation toward said window; said detector means including infrared radiation detecting means for receiving and detecting infrared radiation from said emitter means as reflected by the window and any moisture or other matter thereon.

36. The assembly of claim 35 wherein said infrared radiation emitting means include pulsing means for emitting pulses of infrared radiation toward the window.

37. The assembly of claim 35 wherein said infrared radiation means include at least one infrared energy emitting diode.

38. The assembly of claim 37 including a plurality of infrared energy emitting diodes for emitting infrared energy in a common direction, said monitoring means including means for simultaneously monitoring and detecting the energy output from all of said diodes whereby the average energy output from all said diodes is detected 39. The assembly of claim 38 wherein said support means includes an aperture for mounting each of said diodes; said means for simultaneously monitoring said diodes include a slot communicating with each of said diode mounting apertures.

40. The assembly of claim 35 wherein said monitoring means include an infrared energy sensing means for receiving and detecting infrared radiation.

41. The assembly of claim 40 wherein said detector means and monitoring means each include an infrared energy sensor, said detector cell and monitoring cell being mounted in said support means at separate positions spaced from said emitter means.

42. The assembly of claim 41 wherein said ambient energy sensing means include an infrared energy sensor mounted adjacent said detector sensor at a position spaced from said monitoring sensor in said support means.

43. The assembly of claim 42 including a collimator mounted intermediate the window and said ambient energy sensor for limiting the field of view of infrared energy entering said ambient energy sensor by allowing only that infrared energy which is substantially parallel to the reflection angle to impinge on said ambient sensor.

44. The assembly of claim 43 including a filter for preventing radiant energy below a predetermined wavelength from reaching said ambient sensor, said filter being mounted in said support means intermediate said collimator and said ambient sensor.

45. The assembly of claim 40 wherein said monitoring means and ambient energy sensing means are combined and include an infrared energy sensor mounted in said support means adjacent said detector sensor.

46. The assembly of claim 45 wherein said monitoring and ambient energy sensor is generally planar and is mounted generally perpendicular to said reflection angle.

47. The assembly of claim 34 including a collimator mounted on said support means intermediate the window and said ambient energy sensing means for limiting the field of view of radiant energy entering said ambient energy sensing means and allowing only that radiant energy which is substantially parallel to the reflection angle to impinge on said ambient energy sensing means; and a filter mounted on said support means between said collimator and ambient energy sensing means for preventing radiant energy below a predetermined wavelength from reaching said ambient energy sensing means.

48. The assembly of claim 34 including a circuit board mounted on said support means, said circuit board including circuit elements for controlling operation of said emitter means, detector means, monitoring means and ambient energy sensing means.

* * * * *

UNITED STATES PATENT AND TRADEMARK OFFICE
CERTIFICATE OF CORRECTION

PATENT NO. : 4,871,917

DATED : October 3, 1989

INVENTOR(S) : Desmond J. O'Farrell et al.

It is certified that error appears in the above-identified patent and that said Letters Patent is hereby corrected as shown below:

Column 1, line 53/54:

"$)^{1/2}$" should be --$)^{-1/2}$--.

Column 5, line 22:

"An" should be --Any--.

Column 6, line 44:

"a" should be --as--.

Column 12, line 52:

"s" should be --so--.

Column 13, line 38:

"cove" should be --cover--.

Column 13, line 59:

"form" should be --forms--.

Column 14, claim 1, line 23:

"deflector" should be --detector--.

Column 16, claim 17, line 48:

"an" should be --any--.

UNITED STATES PATENT AND TRADEMARK OFFICE
CERTIFICATE OF CORRECTION

PATENT NO. : 4,871,917

DATED : October 3, 1989

INVENTOR(S) : Desmond J. O'Farrell et al.

It is certified that error appears in the above-identified patent and that said Letters Patent is hereby corrected as shown below:

Column 18, claim 30, line 18:

After "surface;" insert

--housing means for releasably supporting and enclosing said sensing unit on a vehicle window; and wire cover means for covering and shielding any electrical wires which extend from said sensing unit to other portions of the vehicle;

said housing means including an aperture therethrough for receiving a rearview mirror support; said moisture sensing unit being mounted in said housing means on one side of said aperture, said wire cover means extending on the opposite side of said aperture toward the interior roof headliner area of the vehicle.--.

UNITED STATES PATENT AND TRADEMARK OFFICE
CERTIFICATE OF CORRECTION

PATENT NO. : 4,871,917

DATED : October 3, 1989

INVENTOR(S) : Desmond J. O'Farrell et al.

PAGE 3 OF 3

It is certified that error appears in the above-identified patent and that said Letters Patent is hereby corrected as shown below:

Column 19, claim 38, line 29:

After "detected" insert --.--.

Signed and Sealed this

Sixth Day of November, 1990

Attest:

HARRY F. MANBECK, JR.

*Attesting Officer*      *Commissioner of Patents and Trademarks*